United States Patent [19]

Aghion

[11] Patent Number: 4,976,714

[45] Date of Patent: Dec. 11, 1990

[54] UNIVERSAL INTRAMEDULLARY NAIL, PARTICULARLY FOR THE THIGHBONE

[75] Inventor: Michael Aghion, Courbevoie, France

[73] Assignee: Michael's France, Neuilly, France

[21] Appl. No.: 375,464

[22] Filed: Jul. 5, 1989

[30] Foreign Application Priority Data

Jul. 7, 1988 [FR] France ............................ 88 09202

[51] Int. Cl.⁵ ................................................ A61F 5/04
[52] U.S. Cl. ............................................................ 606/62
[58] Field of Search ........ 128/92 YK, 92 YV, 92 YZ, 128/92 YY, 92 YT, 92 YF, 92 YE

[56] References Cited

U.S. PATENT DOCUMENTS

| 2,265,208 | 12/1941 | Thompson | 128/92 YK |
| 3,893,196 | 7/1975 | Hochman | 128/92 YK |
| 4,682,590 | 7/1987 | Kothmann | 128/92 YV |

FOREIGN PATENT DOCUMENTS

| 824239 | 12/1951 | Fed. Rep. of Germany | 128/92 YZ |
| 767879 | 4/1954 | Fed. Rep. of Germany | 128/92 YZ |
| 913228 | 6/1954 | Fed. Rep. of Germany | 128/92 YZ |
| 893401 | 6/1944 | France | 128/92 YZ |
| 1031128 | 6/1953 | France | 128/92 YZ |

*Primary Examiner*—Robert A. Hafer
*Assistant Examiner*—Kerry Owens
*Attorney, Agent, or Firm*—Young & Thompson

[57] ABSTRACT

The invention relates to a universal intramedullary nail, particularly for the thighbone.

The intramedullary nail according to the invention is characterized by the fact that it is made of at least one profile of constant section and resiliently deformable in the transverse direction, said section being, when at rest, substantially inscribed within a circumference and having the general shape of a U occupying more than one-half of said circumference, and end of said section ending into a circular enlargement while the other end of said section is ending into a key-shaped enlargement the cavity of which is limited by an arc of a circle complementary to said circular enlargement.

Application to surgery.

12 Claims, 2 Drawing Sheets

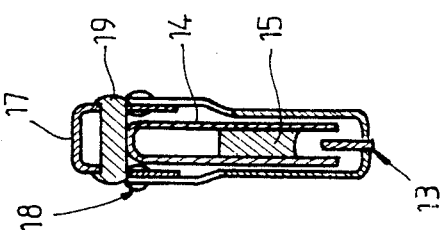
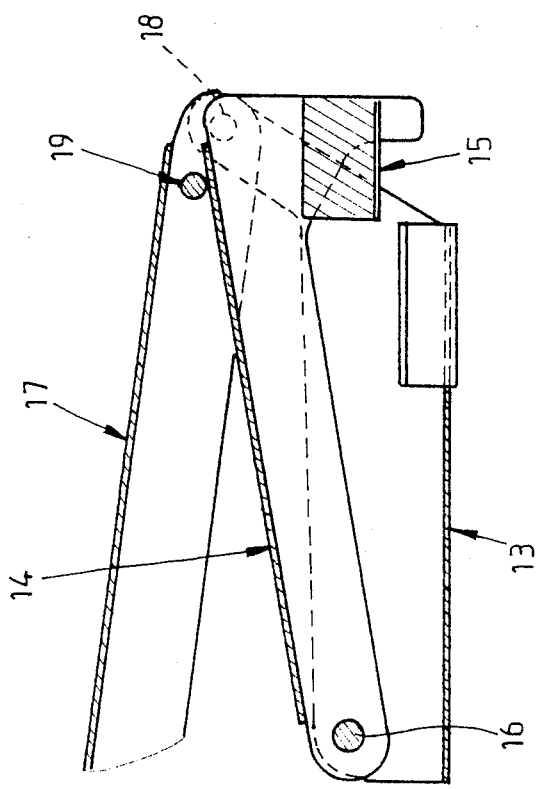

UNIVERSAL INTRAMEDULLARY NAIL, PARTICULARLY FOR THE THIGHBONE

FIELD OF THE INVENTION

The invention relates to a universal intramedullary nail, particularly for the thighbone.

BACKGROUND OF THE INVENTION

Intramedullary nails are used in bone surgery for the obturation of a medullary canal or cavity. Considering the very different diameters and lengths of the canal zone or cavity to seal, according to the type of bone, the age of the patient and the bone region which is concerned, it is necessary to dispose of a medullary nail of determined diameter and length for the operation, which leads to keeping a very large range of nails, of the order of 250 models about. The management and use of such a stock are of course complex and costly.

Moreover, the known nails have often a mechanical strength which is insufficient, particularly in longitudinal compression, which is detremental when putting them in place as well as when they have been set. Such known nails do not allow an anchoring in the medullary canal or cavity walls, thereby limiting their applications.

OBJECTS AND SUMMARY OF THE INVENTION

The present invention aims at remedying the disadvantages of the known medullary nails by providing a new nail of universal usage, necessitating therefore the presence in sotck of only a single model, having a sufficient mechanical strength, particularly in longitudinal compression, while having the required transverse flexibility, and which allows an anchoring in the medullary canal or cavity.

To this effect, the intramedullary nail according to the invention is characterized by the fact that it is made of at least one profile of constant section and resiliently deformable in the transverse direction, said section being, when at rest, substantially inscribed with a circumference and having the general shape of a U occupying more than one half of said circumference, and end of said section ending into a circular enlargement and the other end of said section ending into a key-shaped enlargement the cavity of which is limited by an arc of a circle complementary to said circular enlargement.

The shape and resiliency of the nail according to the invention allow very different ways of using it, according to the diameter of the section to be sealed. For smaller diameters, the profile can be used alone, its transverse resiliency allowing bringing together the edges formed by the enlargments of its transverse section, for providing the required diameter. Generally, the nail is composed of several identical profiles which can be brought together either concentrically, with an identical section, or head to tail, with a reverse section, the cylindrical overthickness of a profile being accommodated within the cavity of the key of another profile.

Advantageously and in order to allow an anchoring when necessary, one at least of the edges of the cavity of the key-shaped end has a sharp edge.

The profile according to the invention is cut to the required length by means of pliers formed of a support tool for the profile, a cutting blade articulated on said support tool and provided with a cutting block, and an actuating lever articulated on said support tool and including a pin which bears on said cutting blade.

For making easy the choice of its length, the profile bears length marks.

Advantageously the profile is formed with equidistant holes, used for the extraction of the nail, affording the certainty that such a hole is always adjacent the free end once it has been cut to length.

The profile can be metallic, preferably in stainless steel. One can also use cobalt-chromium-molybdenum alloys, titanium, aluminium alloys, etc. Advantageously, a metallic profile is produced by drawing.

It can also be produced by extrusion of a synthetic material reinforced with longitudinal fibers, for example glass, carbon, kevlar fibers, etc.

For making easier the introduction of the nail, one can provide both ends of the profile with a taper forming an elongated cone. An inlet conical end remains available after the profile has been cut to length and the remaining portion can be used, according to its length, for another operation, with an inlet conical end.

BRIEF DESCRIPTION OF DRAWINGS

The invention will be better understood from the reading of the following description made with reference to the accompanying drawings wherein:

FIG. 3 is a side elevation view of cutting pliers for the profile of FIGS. 1 and 2; and FIG. 4 is a transverse sectional view of the pliers of FIG. 3.

DETAILED DESCRIPTION OF THE INVENTION

Figure 2:
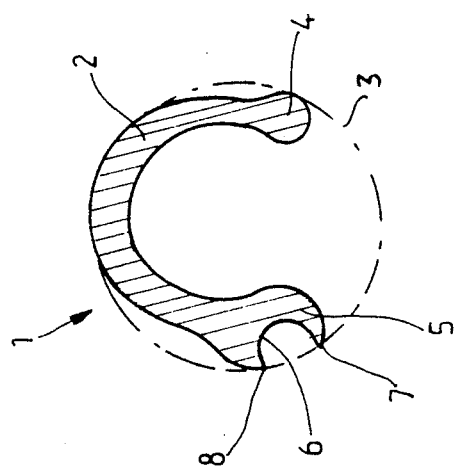
FIG. 2 is a transverse sectional view of the profile of FIG. 1.
Figure 1:
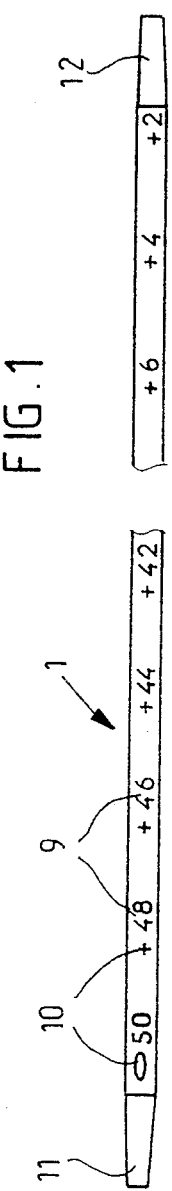
FIG. 1 is a plan schematic view of a profile according to an embodiment of the invention.

According to the present invention, an intramedullary nail is formed of at least one profile 1 an embodiment of which is shown in FIGS. 1 and 2. Profile 1 is of a constant section 2, resiliently deformable in the transverse direction, which is, in the position shown in FIG. 2, inscribed inside a circumference 3. Section 2 has the general shape of a U occupying more than one half of circumference 3. An end of section 2 terminates in a circular enlargement 4 and the other end terminates in an enlargement in the shape of a key 5. Cavity 6 of key 5 is formed by an arc of a circle of the same radius as the circumference of the circular enlargement 4, meaning that this cavity 6 is complementary to the circular enlargement 4.

In the example described, points 7 and 8 of pliers 5 have a sharp edge, thereby allowing an anchoring of the nail in the bone wall of the medullary cavity where it is implanted.

Profile 1 bears marks 9 which are an indication of its length and is formed with oblong and equidistant holes 10. After having been cut to the chosen length by using pliers which will be described with reference to FIGS. 3 and 4, a hole 10 is always adjacent the cut end and can be used for extracting the nail by means of a hook (not shown).

Moreover, both ends 11, 12 of profile 1 are, in the example shown, machined with a chamfer forming an elongated cone to make the introduction of the nail easy. Once the profile 1 has been cut to length, the remaining portion may be used, provided its length is sufficient, with the remaining introduction cone 11, 12.

The profile may be made of metal, preferably stainless steel. It may also be made of a cobalt-chromium-molybdenum alloy, titanium, an aluminium alloy or any other convenient metal or metallic alloy. The metallic profile can be produced by drawing.

Profile 1 can also be made of a synthetic material reinforced with longitudinal fibers having a high modulus of elasticity such as glass, carbon, kevlar fibers, etc. It is advantageously produced by extrusion in a die of convenient profile. It can be opaque to X-rays so as not to disturb an X-ray examination.

For sealing small cavities having a section less than circumference 3, the nail is made of a single profile 1 radially compressed by bringing its end enlargements 4 and 5 nearer to each other.

For cavities having a section larger than circumference 3, one will use two profiles 1 or more. The profiles 1 may then be placed concentrically while being successively fitted into one another. According to another embodiment, they are mounted head to tail, meaning that the enlargement of circular section 4 of a profile 1 is accommodated inside the cavity 6 of the enlargement 5 of profile 1, and thus step by step. Thereby is obtained a cylindrical rule assembly authorizing an angular freedom which is favourable for the creation of the circumscribed diameters to the composite nail. In all cases, the radial resiliency of profiles 1 allows matching the various progressive sections of the intramedullary cavity.

Once it has been set to the right length, the cut-out end has a complete section 2, which makes easy the impact of a hammer on the nail to be driven in.

The multiplicity of profiles 1 forming the nail is favourable to a good mechanical behaviour due to the freedom of assembly of each profile to which no longitudinal stress is applied.

When the profile 1 is metallic, the length marks 9 can be formed by using a laser. When profile 1 is made of a plastic material, one can use an ink.

The shape of section 2 is not limited to the example shown. In particular, it may include longitudinal planar facets.

With the nail according to the invention, and in addition to its perfect adaptation to the intramedullary cavity, the use of the basic profile 1 is made easy by the fact that the only thing the user has to do is to choose the number of identical profiles 1 as a function of the transverse dimension of the cavity to seal, and to cut them to the required length.

This setting to the right length is made easy by the use of a special tool shown in FIGS. 3 and 4. This tool is made of a support 13 for profile 1, of a cutting blade 14 fitted out with a cutting block 15 swivelable with respect to block 3 about an axis 16, and an actuating lever 17 articulated on support 13 about an axis 18 and including a pin 19 bearing on blade 14. The tool can be operated manually, hydraulically, pneumatically, electrically, etc.

I claim:

1. A universal intramedullary nail, particular for the thigh-bone, comprising a profile of constant section and resiliently deformable in the transverse direction, said section being, when at rest, sustantially inscribed within a circumference of a circle and having the general shape of a U occupying more than one half of said circumference, an end of said section ending in a circular enlargement while the other end of said section ends in an enlargement having a circular cavity complementary to said circular enlargement.

2. An intramedullary nail according to claim 1, characterized by the fact that at least one of the edges of said cavity of the key-shaped end has a sharp edge.

3. An intramedullary nail according to claim 1, wherein said profile bears length marks.

4. An intramedullary nail according to claim 1, wherein said profile is formed with equidistant holes.

5. An intramedullary nail according to claim 1, wherein said profile is metallic.

6. An intramedullary nail according to claim 5, wherein said metallic profile is an extrusion.

7. An intramedullary nail according to claim 1, wherein said profile is a synthetic material reinforced with longitudinal fibers having a high modulus of elasticity.

8. An intramedullary nail according to claim 7, wherein said profile of a reinforced synthetic material is an extrusion.

9. An intramedullary nail according to claim 1, wherein both ends of said profile are formed with a chamfer forming an elongated cone.

10. An intramedullary nail according to claim 1, wherein said profile is made of a material opaque to X-rays.

11. An intramedullary nail according to claim 1, which includes at least two profiles placed concentrically.

12. An intramedullary nail according to claim 1, which includes at least two profiles, the enlargement of circular section of one profile being accommodated within the cavity of the key-shaped enlargement of an adjacent profile.

* * * * *